(12) United States Patent
Dou et al.

(10) Patent No.: US 12,233,078 B2
(45) Date of Patent: Feb. 25, 2025

(54) METHOD AND KIT FOR ANALYSIS OF DRUG RESISTANCE OF TUMOR CELLS

(71) Applicant: Shanghai Jiao Tong University, Shanghai (CN)

(72) Inventors: Hongjing Dou, Shanghai (CN); Lingshan Liu, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 53 days.

(21) Appl. No.: 17/837,417

(22) Filed: Jun. 10, 2022

(65) Prior Publication Data

US 2022/0395518 A1 Dec. 15, 2022

(30) Foreign Application Priority Data

Jun. 11, 2021 (CN) .......................... 202110654859.4

(51) Int. Cl.
*A61K 31/695* (2006.01)
*A61K 9/14* (2006.01)
(Continued)

(52) U.S. Cl.
CPC .............. *A61K 31/695* (2013.01); *A61K 9/14* (2013.01); *A61K 47/6933* (2017.08); *G01N 33/574* (2013.01)

(58) Field of Classification Search
CPC .... A61K 31/695; A61K 9/14; A61K 47/6933; G01N 33/574; G01N 2500/10; G01N 33/5011; G01N 21/6486; G01N 21/01
See application file for complete search history.

(56) References Cited

U.S. PATENT DOCUMENTS

2012/0225421 A1* 9/2012 Richardson .......... C12Q 1/6869
435/5

FOREIGN PATENT DOCUMENTS

CN 111440840 A 7/2020

OTHER PUBLICATIONS

Sun Y, Zheng L, Yang Y, Qian X, Fu T, Li X, Yang Z, Yan H, Cui C, Tan W. Metal-Organic Framework Nanocarriers for Drug Delivery in Biomedical Applications. Nanomicro Lett. May 2, 2020;12(1):103. doi: 10.1007/s40820-020-00423-3. PMID: 34138099; PMCID: PMC7770922. (Year: 2020).*

(Continued)

*Primary Examiner* — Jeffrey H Murray
*Assistant Examiner* — Kevin S Martin
(74) *Attorney, Agent, or Firm* — Fitch, Even, Tabin & Flannery, LLP

(57) ABSTRACT

The present invention discloses a method for analysis of drug resistance of tumor cells. The method includes the steps of: (a) providing silicon dioxide nanoparticles, polystyrene-co-polyacrylic acid nanoparticles or metal-organic framework nanoparticles; (b) co-incubating the silicon dioxide nanoparticles, the polystyrene-co-polyacrylic acid nanoparticles or the metal-organic framework nanoparticles with the tumor cells; and (c) detecting endocytosis of the silicon dioxide nanoparticles, the polystyrene-co-polyacrylic acid nanoparticles or the metal-organic framework nanoparticles by the tumor cells. The analysis method of the present invention can analytically identify drug-resistant tumor cells in a clear, intuitive and efficient way. The provided nanoparticles feature simple synthesis processes that take short periods of time, and after they are co-incubated with the tumor cells, a flow cytometer is used for detection. Based on a result of the detection, a degree of drug-resistance of the tumor cells and a proportion of drug-resistant cells therein are determined, making the method simple and efficient.

9 Claims, 1 Drawing Sheet

(51) Int. Cl.
  *A61K 47/69*   (2017.01)
  *G01N 33/574*  (2006.01)
  *G01N 21/01*   (2006.01)
  *G01N 21/64*   (2006.01)
  *G01N 33/50*   (2006.01)

(56) References Cited

OTHER PUBLICATIONS

Wang C, Wang F, Zhang J, Liu L, Xu G, Dou H. Fluorescent Polysaccharide Nanogels for the Detection of Tumor Heterogeneity in Drug-Surviving Cancer Cells. Adv Biosyst. Feb. 2020;4(2):e1900213. doi: 10.1002/adbi.201900213. Epub Dec. 5, 2019. PMID: 32293135. (Year: 2020).*

Cecil Textbook of Medicine, vol. 1, Edition 20, 1997 (Year: 1997).*

China National Intellectual Property Administration, Decision of Rejection mailed Aug. 3, 2022 in Chinese Application No. 2021106548594 and English Translation, 9 pages.

Vigderman, Leonid, et al., "Therapeutic platforms based on gold nanoparticles and their covalent conjugates with drug molecules," Advanced Drug Delivery Reviews, 65 (2013) 663-676.

Dixit, Suraj, et al., "Transferrin receptor-targeted theranostic gold nanoparticles for photosensitizer delivery in brain tumors," Nanoscale, 7 (2015) 1782-1790.

Chen, Jiaming, et al., "The exploration of endocytic mechanisms of PLA-PEG nanoparticles prepared by coaxialtri-capillary electrospray-template removal method," Colloids and Surfaces B: Biointerfaces, 161 (2018) 10-17.

* cited by examiner

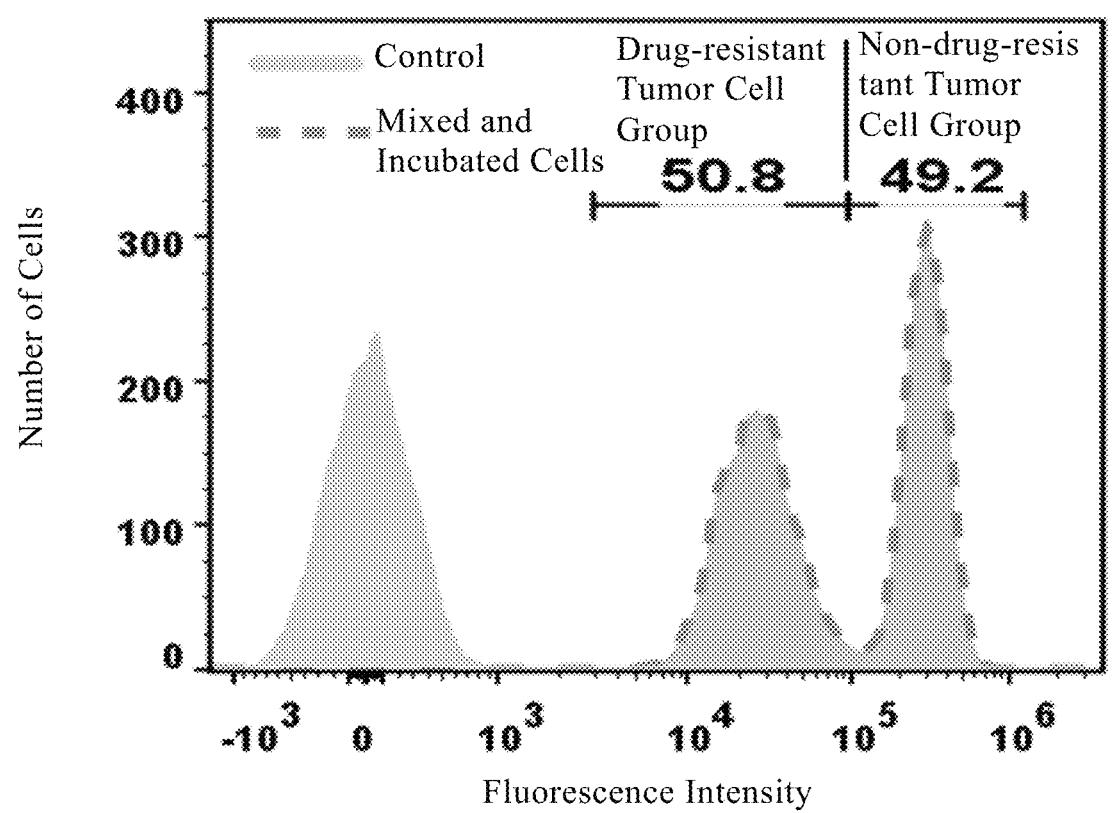

METHOD AND KIT FOR ANALYSIS OF DRUG RESISTANCE OF TUMOR CELLS

CROSS-REFERENCE TO RELATED APPLICATIONS

This application claims priority from Chinese Patent Application Number 202110654859.4, filed Jun. 11, 2021.

FIELD OF THE INVENTION

The present invention relates to the field of tumor analysis and treatment and, in particular to, a method and kit for analysis of drug resistance of tumor cells.

DESCRIPTION OF THE PRIOR ART

Cancer is a problem that threatens human lives and health all over the world. At present, treatment methods for cancer mainly include chemotherapy, radiotherapy and immunotherapy, among others. However, in the process of cancer treatment, there always develop different degrees of drug resistance, which lowers cancer treatment effects. Multidrug resistance that develops during chemotherapy is a major challenge faced by tumor chemotherapy. Multidrug resistance to chemotherapy may be attributed to many causes, and the most common one is that the expression of P-glycoprotein leads to a chemotherapeutic drug being pumped out of cells, making it impossible for the chemotherapeutic drug to accumulate in the cells to a concentration that kills the cells to provide a therapeutic effect. Therefore, for multidrug resistance to tumor chemotherapy, it is of great significance to analyze drug-resistant cells and non-drug-resistant cells.

Chinese patent CN111440840A discloses a method for analyzing drug resistance of tumor cells using polysaccharide-based nanoparticles. However, such hydrophilic nanoparticles are limited in crossing of cell membranes that are fat-soluble. Moreover, these nanoparticles require complicated synthesis processes that are demanding on experimental conditions and time-consuming.

In view of the drawbacks of the prior art, the inventors introduce nanoparticles with different surface properties, which are silicon dioxide nanoparticles, polystyrene-co-polyacrylic acid nanoparticles and metal-organic framework nanoparticles. These nanoparticles feature simple synthesis processes, short post-processing times and surface properties that are more favorable to cell membrane crossing and cellular endocytosis. Nanoparticles may be fluorescently labeled or surface modified to gain the ability to enable analysis of drug-resistant tumor cells by means of specific endocytosis. Using this as a means to study development and progression mechanisms of tumor drug resistance and interaction mechanisms between drug-resistant and non-drug-resistant tumor cells will be of great utility value for both cancer diagnosis and treatment.

SUMMARY OF THE INVENTION

In view of the above-described shortcomings of the prior art, the technical problem to be solved by the present invention is how to analytically identify drug-resistant tumor cells in a simpler and more efficient way.

In order to achieve the above goal, the present invention provides a method for analysis of drug resistance of tumor cells, which includes the step of applying silicon dioxide nanoparticles, polystyrene-co-polyacrylic acid nanoparticles or metal-organic framework nanoparticles to the tumor cells.

Further, the method includes the steps of:
(a) providing the silicon dioxide nanoparticles, the polystyrene-co-polyacrylic acid nanoparticles or the metal-organic framework nanoparticles;
(b) co-incubating the silicon dioxide nanoparticles, the polystyrene-co-polyacrylic acid nanoparticles or the metal-organic framework nanoparticles with the tumor cells; and
(c) detecting endocytosis of the silicon dioxide nanoparticles, the polystyrene-co-polyacrylic acid nanoparticles or the metal-organic framework nanoparticles by the tumor cells.

Further, the metal-organic framework nanoparticles include ZIF-8 nanoparticles, ZIF-70 nanoparticles, ZIF-90 nanoparticles, etc.

Further, the method further includes step (d) prior to step (b), and step (d) is to modify the silicon dioxide nanoparticles, the polystyrene-co-polyacrylic acid nanoparticles or the metal-organic framework nanoparticles with fluorescent molecules.

Further, the fluorescent molecules in step (d) are selected from one or more of fluorescein, rhodamines, cyanine dyes, coumarin and fluorescent inorganic nanocrystals.

Further, the silicon dioxide nanoparticles, the polystyrene-co-polyacrylic acid nanoparticles or the metal-organic framework nanoparticles react with the fluorescent molecules at a mass ratio of 20-2000:1.

Further, in step (b), the silicon dioxide nanoparticles, the polystyrene-co-polyacrylic acid nanoparticles or the metal-organic framework nanoparticles are co-incubated with the tumor cells for 0.5-4 h.

Further, drug-resistant tumor cells include any one of paclitaxel-resistant human lung cancer (A549) cells, cisplatin-resistant human lung cancer (A549) cells, adriamycin-resistant human lung cancer (A549) cells, oxaliplatin-resistant human lung cancer (A549) cells, gefitinib-resistant human lung adenocarcinoma (PC-9) cells, paclitaxel-resistant human leukemia (K562) cells, cisplatin-resistant human leukemia (K562) cells, adriamycin-resistant human leukemia (K562) cells, vincristine-resistant human colon cancer (HCT-8) cells, paclitaxel-resistant human colon cancer (HCT-8) cells, fluorouracil-resistant human colon cancer (HCT-8) cells, oxaliplatin-resistant human colon cancer (HCT116) cells, adriamycin-resistant human colon cancer (LoVo) cells, cisplatin-resistant human colon cancer (HT-29) cells, paclitaxel-resistant human breast cancer (MCF-7) cells, cisplatin-resistant human breast cancer (MCF-7) cells, adriamycin-resistant human breast cancer (MCF-7) cells, liposomal doxorubicin-resistant human breast cancer (MCF-7) cells, adriamycin-resistant human breast cancer (MDA-MB-231) cells, cisplatin-resistant human ovarian cancer (COC1) cells, cisplatin-resistant human ovarian cancer (A2780) cells, paclitaxel-resistant human ovarian cancer (A2780) cells, paclitaxel-resistant human ovarian cancer (SKOV3) cells, cisplatin-resistant human ovarian cancer (SKOV3) cells, fluorouracil-resistant human liver cancer (Bel) cells, cisplatin-resistant human liver cancer (SMMC7721) cells, cisplatin-resistant human gastric cancer (SGC7901) cells, cisplatin-resistant human squamous-cell lung carcinoma (SK-MES-1) cells, fluorouracil-resistant human pancreatic cancer (PATU-8988) cells, cisplatin-resistant human pancreatic cancer (Bxpc3) cells, adriamycin-resistant human bladder cancer (BIU-87) cells, paclitaxel-resistant human cervical cancer (Hela) cells, cisplatin-resistant human cervical cancer (Hela) cells, adriamycin-resistant human cervical cancer (Hela) cells, cisplatin-resistant human nasopharyngeal carcinoma (CNE2) cells, cisplatin-resistant human malignant melanoma (A375) cells and cisplatin-resistant human bladder transitional cell carcinoma (T-24) cells.

Further, non-drug-resistant tumor cells include any one of human lung cancer (A549) cells, human leukemia (K562) cells, human colon cancer (HCT-8) cells, human colon cancer (HCT116) cells, human colon cancer (LoVo) cells, human colon cancer (HT-29) cells, human breast cancer (MCF-7) cells, human breast cancer (MDA-MB-231) cells, human ovarian cancer (COC1) cells, human ovarian cancer (A2780) cells, human ovarian cancer (A2780) cells, human ovarian cancer (SKOV3) cells, human liver cancer (Bel) cells, human liver cancer (SMMC7721) cells, human gastric cancer (SGC7901) cells, human squamous-cell lung carcinoma (SK-MES-1) cells, human pancreatic cancer (PATU-8988) cells, human pancreatic cancer (Bxpc3) cells, human bladder cancer (BIU-87) cells, human cervical cancer (Hela) cells, human cervical cancer (Hela) cells, human cervical cancer (Hela) cells, human nasopharyngeal carcinoma (CNE2) cells, human malignant melanoma (A375) cells and human bladder transitional cell carcinoma (T-24) cells.

The present invention also provides a kit for analysis of drug resistance of tumor cells, which includes silicon dioxide nanoparticles, polystyrene-co-polyacrylic acid nanoparticles or metal-organic framework nanoparticles.

Further, the metal-organic framework nanoparticles include ZIF-8 nanoparticles, ZIF-70 nanoparticles and ZIF-90 nanoparticles.

Further, the silicon dioxide nanoparticles, the polystyrene-co-polyacrylic acid nanoparticles or the metal-organic framework nanoparticles are modified with fluorescent molecules.

Further, the fluorescent molecules are selected from one or more of fluorescein, rhodamines, cyanine dyes, coumarin and fluorescent inorganic nanocrystals.

Technical Effects

The analysis method of the present invention can analytically identify drug-resistant tumor cells in a clear, intuitive and efficient way.

The nanoparticles provided in the present invention feature simple synthesis processes that take short periods of time, and after they are co-incubated with the tumor cells, a flow cytometer is used for detection. Based on a result of the detection, a degree of drug-resistance of the tumor cells and a proportion of drug-resistant cells therein are determined, making the method simple and efficient.

Below, the concept, structural details and resulting technical effects of the present invention will be further described with reference to the accompanying drawing to provide a full understanding of the objects, features and effects of the invention.

BRIEF DESCRIPTION OF THE DRAWING

The FIGURE is a diagram showing fluorescence intensity results of tumor drug-resistant cells and non-drug-resistant cells according to a preferred embodiment of the present invention.

DETAILED DESCRIPTION OF THE PREFERRED EMBODIMENTS

Below, the accompanying drawing of this specification is referenced to introduce multiple preferred embodiments of the present invention so that the techniques thereof become more apparent and readily understood. The present invention may be embodied in many different forms of embodiment, and the protection scope of the invention is not limited only to the embodiments mentioned herein.

I. Preparation of Nanoparticles

Example 1

0.25 g of zinc nitrate hexahydrate ($Zn(NO_3)_2 \cdot 6H_2O$) was dissolved in 1 mL of water and 2.5 g of dimethylimidazole was dissolved in 10 mL of water to obtain a zinc nitrate hexahydrate solution and a dimethylimidazole solution, respectively. Cyanine5.5 N-hydroxysuccinimide (Cy5.5-NHS) was dissolved in dimethyl sulfoxide (DMSO) to form a Cy5.5-NHS solution in DMSO (Cy5.5-NHS DMSO solution) with a concentration of 0.5 mg/mL. 1 mL of the zinc nitrate hexahydrate solution, a total volume of 7.7 mL of the Cy5.5-NHS DMSO solution and 3.3 mL of deionized water were added to a reaction vessel, and the reaction was stirred at room temperature for 30 min. The concentration of the Cy5.5-NHS DMSO solution was adjusted according to a mass ratio of 20-2000:1 of nanoparticles to the fluorescein. Subsequently, 10 mL of the dimethylimidazole solution was added, and the reaction was continued under stirring at room temperature for 1 h. The resulting product was collected by centrifugation at 12000 rpm for 20 min and then washed by centrifugation three times with deionized water, and Cy5.5-labeled ZIF-8 nanoparticles were obtained.

Example 2

4.9 mg of fluorescein isothiocyanate (FITC) was added to 0.68 mL of (3-aminopropyl)trimethoxysilane (APTMS), followed by the addition of 6.95 mL of ethanol. After stirring for 24 h away from light, the product FITC-APTMS was obtained. FITC-APTMS, 1 mL of tetraethyl orthosilicate (TEOS), 5 mL of 28 wt % aqueous ammonia and 50 mL of ethanol were added to a reaction flask, and the reaction was stirred at room temperature away from light for 10 h. The amount of FITC-APTMS was adjusted according to a mass ratio of 20-2000:1 of nanoparticles to the fluorescein. After the reaction ended, the product was collected by centrifugation and washed by centrifugation three times with ethanol, and FITC-labeled $SiO_2$ nanoparticles were obtained.

Example 3

180 μL of acrylic acid and 45 mL of deionized water were added to a reactor and stirred at room temperature until dissolution was achieved. 880 μL of styrene was then added, and nitrogen was passed for 30 min, followed by the addition of 0.03 g of potassium persulfate (being dissolved in 5 mL of deionized water). The system was then heated to 70° C., and the reaction was stirred for 8 h under a nitrogen atmosphere. After the reaction ended, the product was collected by centrifugation and washed three times with deionized water, and PS-co-PAA nanoparticles were obtained.

The obtained PS-co-PAA nanoparticles were dissolved in a pH 5.5 MES buffer to obtain a PS-co-PAA solution with a concentration of 3 mg/mL. 6.4 mg of 1-ethyl-(3-dimethylaminopropyl)carbodiimide hydrochloride (EDC·HCl) was added to 50 mg of the PS-co-PAA solution, and stirring was conducted at room temperature for 10 min. Subsequently, 17.9 mg of N-hydroxysulfosuccinimide (sulfo-NHS)

sodium salt was added, and the reaction was continued for 3 h. After that, 5-aminofluorescein (5-AF) was added, and the reaction was continued away from light until 24 h. The amount of 5-AF was adjusted according to a mass ratio of 20-2000:1 of nanoparticles to the fluorescein. After the reaction ended, the product was collected by centrifugation and washed three times with deionized water, and 5-AF-labeled PS-co-PAA nanoparticles were obtained.

II. Analysis of Drug Resistance of Tumor Cells Using Nanoparticles

Example 4

Paclitaxel-resistant and non-drug-resistant human lung cancer (A549) cells were mixed and seeded in a six-well plate. When the cells adhered and grew to 70-80% confluence, the spent culture medium was aspirated, and each well was added with 2 mL of a culture medium containing 100 μL of the Cy5.5-labeled ZIF-8 nanoparticles. Incubation was continued in an incubator for 2 h. The cells were detached, collected, and washed by centrifugation twice with 500 g of phosphate buffered saline, 5 min each time. Finally, they were re-suspended in 500 μL of phosphate buffered saline and detected on a flow cytometer. A fluorescence intensity comparison was drawn between the paclitaxel-resistant and non-drug-resistant human lung cancer (A549) cells, as shown in the FIGURE. The paclitaxel-resistant human lung cancer (A549) cells displayed lower fluorescence intensity than the non-drug-resistant cells and were present at a percentage of 50.8%.

Example 5

Paclitaxel-resistant and non-drug-resistant human leukemia (K562) cells were mixed and seeded in a six-well plate. After co-incubation for 12-24 h, each well was added with 2 mL of a culture medium containing 100 μL of the Cy5.5-labeled ZIF-8 nanoparticles. Incubation was continued in an incubator for 2 h. The cells were collected and washed by centrifugation twice with 500 g of a phosphate buffer solution, 5 min each time. Finally, they were re-suspended in 500 μL of phosphate buffered saline and detected on a flow cytometer. A fluorescence intensity comparison was drawn between the paclitaxel-resistant and non-drug-resistant human leukemia (K562) cells. The paclitaxel-resistant human leukemia (K562) cells displayed lower fluorescence intensity than the non-drug-resistant cells.

Example 6

Adriamycin-resistant and non-drug-resistant human leukemia (K562) cells were mixed and seeded in a six-well plate. After co-incubation for 12-24 h, each well was added with 2 mL of a culture medium containing 100 μL of the FITC-labeled SiO$_2$ nanoparticles. Incubation was continued in an incubator for 2 h. The cells were collected and washed by centrifugation twice with 500 g of a phosphate buffer solution, 5 min each time. Finally, they were re-suspended in 500 μL of phosphate buffered saline and detected on a flow cytometer. A fluorescence intensity comparison was drawn between the adriamycin-resistant and non-drug-resistant human leukemia (K562) cells. The adriamycin-resistant human leukemia (K562) cells displayed lower fluorescence intensity than the non-drug-resistant cells.

Example 7

Paclitaxel-resistant and non-drug-resistant human breast cancer (MCF-7) cells were mixed and seeded in a six-well plate. They were then incubated overnight to adhere. When the cells grew to 70-80% confluence, the culture medium in each well was replaced with 2 mL of a culture medium containing 100 μL of the 5-AF-labeled PS-co-PAA nanoparticles. Incubation was continued in an incubator for 2 h. The cells were detached, collected, and washed by centrifugation twice with 500 g of phosphate buffered saline, 5 min each time. Finally, they were re-suspended in 500 μL of phosphate buffered saline and detected on a flow cytometer. A fluorescence intensity comparison was drawn between the paclitaxel-resistant and non-drug-resistant human breast cancer (MCF-7) cells. The paclitaxel-resistant human breast cancer (MCF-7) cells displayed lower fluorescence intensity than the non-drug-resistant cells.

Example 8

Vincristine-resistant and non-drug-resistant human colon cancer (HCT-8) cells were mixed and seeded in a six-well plate. They were then incubated overnight to adhere. When the cells grew to 70-80% confluence, the culture medium in each well was replaced with 2 mL of a culture medium containing 100 μL of the 5-AF-labeled PS-co-PAA nanoparticles. Incubation was continued in an incubator for 2 h. The cells were detached, collected, and washed by centrifugation twice with 500 g of phosphate buffered saline, 5 min each time. Finally, they were re-suspended in 500 μL of phosphate buffered saline and detected on a flow cytometer. A fluorescence intensity comparison was drawn between the vincristine-resistant and non-drug-resistant human colon cancer (HCT-8) cells. The vincristine-resistant human colon cancer (HCT-8) cells displayed lower fluorescence intensity than the non-drug-resistant cells.

Example 9

Paclitaxel-resistant and non-drug-resistant human ovarian cancer (A2780) cells were mixed and seeded in a six-well plate. When the cells adhered and grew to 70-80% confluence, the spent culture medium was aspirated, and each well was added with 2 mL of a culture medium containing 100 μL of the FITC-labeled SiO$_2$ nanoparticles. Incubation was continued in an incubator for 2 h. The cells were detached, collected, and washed by centrifugation twice with 500 g of phosphate buffered saline, 5 min each time. Finally, they were re-suspended in 500 μL of phosphate buffered saline and detected on a flow cytometer. A fluorescence intensity comparison was drawn between the paclitaxel-resistant and non-drug-resistant human ovarian cancer (A2780) cells. The paclitaxel-resistant human ovarian cancer (A2780) cells displayed lower fluorescence intensity than the non-drug-resistant cells.

Example 10

Cisplatin-resistant and non-drug-resistant human ovarian cancer (SKOV3) cells were mixed and seeded in a six-well plate. When the cells adhered and grew to 70-80% confluence, the spent culture medium was aspirated, and each well was added with 2 mL of a culture medium containing 100 μL of the Cy5.5-labeled ZIF-8 nanoparticles. Incubation was continued in an incubator for 2 h. The cells were detached, collected, and washed by centrifugation twice with 500 g of phosphate buffered saline, 5 min each time. Finally, they were re-suspended in 500 μL of phosphate buffered saline and detected on a flow cytometer. A fluorescence intensity comparison was drawn between the cisplatin-resistant and non-drug-resistant human ovarian cancer (SKOV3) cells. The cisplatin-resistant human ovarian cancer (SKOV3) cells displayed lower fluorescence intensity than the non-drug-resistant cells.

Example 11

Paclitaxel-resistant and non-drug-resistant human cervical cancer (Hela) cells were mixed and seeded in a six-well plate. When the cells adhered and grew to 70-80% confluence, the spent culture medium was aspirated, and each well was added with 2 mL of a culture medium containing 100 μL of the 5-AF-labeled PS-co-PAA nanoparticles. Incubation was continued in an incubator for 2 h. The cells were detached, collected, and washed by centrifugation twice with 500 g of phosphate buffered saline, 5 min each time. Finally, they were re-suspended in 500 μL of phosphate buffered saline and detected on a flow cytometer. A fluorescence intensity comparison was drawn between the paclitaxel-resistant and non-drug-resistant human cervical cancer (Hela) cells. The paclitaxel-resistant human cervical cancer (Hela) cells displayed lower fluorescence intensity than the non-drug-resistant cells.

Preferred specific embodiments have been described in detail above. It is to be understood that, those of ordinary skill in the art, without the need for creative effort, can make various modifications and changes, based on the concept of the present invention. Accordingly, all the technical solutions that can be obtained by those skilled in the art by logical analysis, inference or limited experimentation in accordance with the concept of the invention on the basis of the prior art are intended to fall within the protection scope as defined by the claims.

The invention claimed is:

1. A method for analysis of drug resistance of tumor cells, comprising the steps of:
    (a) providing silicon dioxide nanoparticles, polystyrene-co-polyacrylic acid nanoparticles or metal-organic framework nanoparticles;
    (b) co-incubating the silicon dioxide nanoparticles, the polystyrene-co-polyacrylic acid nanoparticles or the metal-organic framework nanoparticles with the tumor cells; and
    (c) detecting endocytosis of the silicon dioxide nanoparticles, the polystyrene-co-polyacrylic acid nanoparticles or the metal-organic framework nanoparticles by the tumor cells;
    wherein the tumor cells comprise drug-resistant tumor cells and/or non-drug-resistant tumor cells;
    the drug-resistant tumor cells include at least one of paclitaxel-resistant human lung cancer (A549) cells, paclitaxel-resistant human leukemia (K562) cells, adriamycin-resistant human leukemia (K562) cells, paclitaxel-resistant human breast cancer (MCF-7) cells, vincristine-resistant human colon cancer (HCT-8) cells, paclitaxel-resistant human ovarian cancer (A2780) cells, cisplatin-resistant human ovarian cancer (SKOV3) cells, paclitaxel-resistant human cervical cancer (Hela) cells, and paclitaxel-resistant human ovarian cancer (SKOV3) cells;
    the non-drug-resistant tumor cells include at least one of human lung cancer (A549) cells, human leukemia (K562) cells, human breast cancer (MCF-7) cells, human colon cancer (HCT-8) cells, human ovarian cancer (A2780) cells, human ovarian cancer (SKOV3) cells and human cervical cancer (Hela) cells.

2. The method for analysis of drug resistance of tumor cells as in claim 1, characterized in that the metal-organic framework nanoparticles include ZIF-8 nanoparticles, ZIF-70 nanoparticles and ZIF-90 nanoparticles.

3. The method for analysis of drug resistance of tumor cells as in claim 1, characterized in further comprising step (d) prior to step (b), and step (d) is to modify the silicon dioxide nanoparticles, the polystyrene-co-polyacrylic acid nanoparticles or the metal-organic framework nanoparticles with fluorescent molecules.

4. The method for analysis of drug resistance of tumor cells as in claim 3, characterized in that the fluorescent molecules in step (d) are selected from one or more of fluorescein, rhodamines, cyanine dyes, coumarin and fluorescent inorganic nanocrystals.

5. The method for analysis of drug resistance of tumor cells as in claim 3, characterized in that the silicon dioxide nanoparticles, the polystyrene-co-polyacrylic acid nanoparticles or the metal-organic framework nanoparticles react with the fluorescent molecules at a mass ratio of 20-2000:1.

6. The method for analysis of drug resistance of tumor cells as in claim 1, characterized in that, in step (b), the silicon dioxide nanoparticles, the polystyrene-co-polyacrylic acid nanoparticles or the metal-organic framework nanoparticles are co-incubated with the tumor cells for 0.5-4 h.

7. A kit for analysis of drug resistance of tumor cells, characterized in comprising silicon dioxide nanoparticles modified with fluorescent molecules, polystyrene-co-polyacrylic acid nanoparticles modified with fluorescent molecules or metal-organic framework nanoparticles modified with fluorescent molecules;
    wherein the tumor cells comprise drug-resistant tumor cells and/or non-drug-resistant tumor cells;
    the drug-resistant tumor cells include at least one of paclitaxel-resistant human lung cancer (A549) cells, paclitaxel-resistant human leukemia (K562) cells, adriamycin-resistant human leukemia (K562) cells, paclitaxel-resistant human breast cancer (MCF-7) cells, vincristine-resistant human colon cancer (HCT-8) cells, paclitaxel-resistant human ovarian cancer (A2780) cells, cisplatin-resistant human ovarian cancer (SKOV3) cells, paclitaxel-resistant human cervical cancer (Hela) cells, and paclitaxel-resistant human ovarian cancer (SKOV3) cells;
    the non-drug-resistant tumor cells include at least one of human lung cancer (A549) cells, human leukemia (K562) cells, human breast cancer (MCF-7) cells, human colon cancer (HCT-8) cells, human ovarian cancer (A2780) cells, human ovarian cancer (SKOV3) cells and human cervical cancer (Hela) cells.

8. The kit for analysis of drug resistance of tumor cells as in claim 7, characterized in that the metal-organic framework nanoparticles include ZIF-8 nanoparticles, ZIF-70 nanoparticles and ZIF-90 nanoparticles.

9. The kit for analysis of drug resistance of tumor cells as in claim 7, characterized in that the fluorescent molecules are selected from one or more of fluorescein, rhodamines, cyanine dyes, coumarin and fluorescent inorganic nanocrystals.

* * * * *